(12) United States Patent
Asirvatham et al.

(10) Patent No.: US 12,208,032 B2
(45) Date of Patent: Jan. 28, 2025

(54) THERMAL MODIFICATION TO TREAT CARDIAC ELECTRICAL DISORDERS AND OTHER DISORDERS

(71) Applicant: Mayo Foundation for Medical Education and Research, Rochester, MN (US)

(72) Inventors: Samuel J. Asirvatham, Rochester, MN (US); Paul A. Friedman, Rochester, MN (US); Douglas S. Beinborn, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 324 days.

(21) Appl. No.: 17/531,406

(22) Filed: Nov. 19, 2021

(65) Prior Publication Data

US 2022/0071801 A1   Mar. 10, 2022

Related U.S. Application Data

(63) Continuation of application No. 15/780,719, filed as application No. PCT/US2016/064566 on Dec. 2, 2016, now Pat. No. 11,179,270.

(Continued)

(51) Int. Cl.
*A61F 7/02* (2006.01)
*A61B 5/00* (2006.01)
(Continued)

(52) U.S. Cl.
CPC ............... *A61F 7/02* (2013.01); *A61B 5/361* (2021.01); *A61B 18/14* (2013.01); *A61B 18/1402* (2013.01); *A61B 5/4836* (2013.01); *A61B 2018/00047* (2013.01); *A61B 2018/0016* (2013.01); *A61B 2018/00196* (2013.01);
(Continued)

(58) Field of Classification Search
CPC .......................... A61B 18/1402; A61N 1/0597
See application file for complete search history.

(56) References Cited

U.S. PATENT DOCUMENTS 5,876,422 A    3/1999  van Groeningen
7,840,264 B1  11/2010  Mower
(Continued)

FOREIGN PATENT DOCUMENTS

CN         1747764        3/2006

OTHER PUBLICATIONS

Chorro et al., "Effects of acute reduction of temperature on ventricular fibrillation activation patterns," Am. J. Physiol. Heart Circ. Physiology, 2002, 283:H2331-H2340.
(Continued)

*Primary Examiner* — Kaitlyn E Smith
(74) *Attorney, Agent, or Firm* — Fish & Richardson P.C.

(57) ABSTRACT

Devices and methods are provided for the treatment of pathological conditions including arrhythmias and trauma using temperature modulation via implantable or worn devices. For example, in one example embodiment this document relates to devices and methods for treating atrial or ventricular fibrillation by cooling the epicardium. The devices and methods can also be used to treat other disorders by applying heating and/or cooling to a patient in a number of different manners.

8 Claims, 4 Drawing Sheets

Related U.S. Application Data

(60) Provisional application No. 62/262,786, filed on Dec. 3, 2015.

(51) Int. Cl.
*A61B 5/361* (2021.01)
*A61B 18/00* (2006.01)
*A61B 18/14* (2006.01)
*A61F 7/00* (2006.01)
*A61N 1/362* (2006.01)

(52) U.S. Cl.
CPC .............. *A61B 2018/00214* (2013.01); *A61B 2018/00363* (2013.01); *A61B 2018/00577* (2013.01); *A61B 2018/00613* (2013.01); *A61B 2018/00821* (2013.01); *A61B 2018/00839* (2013.01); *A61F 2007/0075* (2013.01); *A61F 2007/0095* (2013.01); *A61F 2007/0298* (2013.01); *A61N 1/362* (2013.01)

(56) References Cited

U.S. PATENT DOCUMENTS

| | | |
|---|---|---|
| 11,179,270 B2 | 11/2021 | Asirvatham et al. |
| 2002/0151880 A1 | 10/2002 | LaFontaine |
| 2005/0222632 A1 | 10/2005 | Obino |
| 2008/0195161 A1* | 8/2008 | Sakuma ............... A61N 1/0587 607/113 |
| 2013/0012938 A1* | 1/2013 | Asirvatham ............. A61B 5/24 606/41 |
| 2013/0030425 A1 | 1/2013 | Stewart et al. |
| 2013/0184706 A1 | 7/2013 | Gelbart et al. |
| 2015/0216718 A1 | 8/2015 | Diller et al. |
| 2018/0360650 A1 | 12/2018 | Asirvatham et al. |

OTHER PUBLICATIONS

EPO Extended European Search Report in European Application No. 16871559.7 dated Nov. 9, 2018, 98 pages.

PCT International Preliminary Report on Patentability in International Appln. No. PCT/US2016/64566, dated Jun. 5, 2018, 7 pages.

PCT International Search Report and Written Opinion in International Appln. No. PCT/US2016/64566, dated Feb. 17, 2017, 12 pages.

Wathen et al., "Prospective randomized multicenter trial of empirical antitachycardia pacing versus shocks for spontaneous rapid ventricular tachycardia in patients with implantable cardioverter-defibrillators: Pacing Fast Ventricular Tachycardia Reduces Shock Therapies (PainFREE Rx II) trial results," Circulation, Oct. 2004, 110(17):2591-2596.

* cited by examiner

THERMAL MODIFICATION TO TREAT CARDIAC ELECTRICAL DISORDERS AND OTHER DISORDERS

CROSS-REFERENCE TO RELATED APPLICATIONS

This application is a continuation of U.S. application Ser. No. 15/780,719 (issued as U.S. Pat. No. 11,179,270), filed on Jun. 1, 2018, which is a National Stage Application under 35 U.S.C. § 371 that claims the benefit of Application Serial No. PCT/US2016/064566, filed Dec. 2, 2016, which also claims the benefit of U.S. Provisional Application Ser. No. 62/262,786, filed Dec. 3, 2015. The disclosures of the prior applications are considered part of (and are incorporated by reference in) the disclosure of this application.

BACKGROUND

1. Technical Field

This document relates to devices and methods for the treatment of pathological conditions including arrhythmias and trauma using temperature modulation via implantable or worn devices. For example, in one example embodiment this document relates to devices and methods for treating atrial and/or ventricular fibrillation by cooling the epicardium.

2. Background Information

Sudden cardiac arrest is the single largest cause of death of Americans, resulting in more deaths each year than breast cancer, automobile accidents, assault with firearms, cervical cancer, colorectal cancer diabetes, HIV, house fires, prostate cancers and suicides combined (Sudden Cardiac Arrest Foundation, 2014). More than 1,000 Americans die each day from sudden cardiac arrest.

Atrial fibrillation is the most common arrhythmia encountered in clinical practice, affecting over 2.5 million Americans. The risk of atrial fibrillation increases with advancing age, with a lifetime risk of developing the arrhythmia of 25% of all men and women 40 years of age or older. A Mayo Clinic study indicated that the burden of this disease will significantly grow with 16 million Americans expected to be afflicted by 2050.

Multiple prospective randomized trials have demonstrated the clinical benefit of implantable cardiac defibrillators (ICDs) in saving the lives of at-risk individuals, leading to their wide-spread adoption, with the global ICD market estimate to reach $6 billion in 2015 (Trefis, Insight Guru, 2014). A downside associated with ICD therapy, however, is the pain associated with defibrillation, whether shocks are delivered appropriately or inappropriately.

SUMMARY

This document provides devices and methods for the treatment of heart and other conditions using temperature change to prevent or treat arrhythmias or other pathology silage. For example, this document provides devices and methods for treating atrial and ventricular fibrillation by cooling the epicardium. The ability to terminate ventricular fibrillation painlessly has been an extensively sought goal of cardiac defibrillation research. Painless termination of ventricular fibrillation would be advantageous in that inappropriate shocks would cease to be a clinical problem, therapy would be better tolerated, and treatment could be offered to a larger array of at risk individuals.

One potential method for painless defibrillation is the use of cold. Cold temperatures in experimental models have been shown to terminate ventricular fibrillation. This results since the ion channels in cellular membranes responsible for action potential propagation in cardiac syncytium are temperature dependent. This disclosure describes systems and methods that delivers thermal cooling, in isolation or in conjunction with other therapies, to strive towards painless termination of ventricular fibrillation. Moreover, given the painless nature of the therapy (its antiarrhythmic characteristics), it could be given prophylactically when changes in the rhythm develop before true arrhythmia onset, thus preventing arrhythmia onset. Additionally, cooling cardiac tissues changes their conduction properties, potentiating essentially painless therapies. Anti-tachycardia pacing or low energy shock can be used in some embodiments.

This disclosure describes an implantable device that achieves non-destructive rapid and temporary cooling of cardiac tissues for the termination, and potentially prevention, of atrial arrhythmias. The ion channels responsible for propagation of electrical wave fronts through myocardial tissue are temperature sensitive and temperature reduction terminates fibrillatory rhythms. The system includes a percutaneously placed expandable and simply deployed epicardial lead capable of cooling atrial tissues to between 5 to 10 degrees Celsius (or colder in some cases). The use of cold is particularly attractive due to its well-established safety record in cardiac applications. In some embodiments, the epicardial lead will be constructed using an array of thermal electric cooling elements that use the Peltier effect to create a heat differential between opposing surfaces. While some embodiments are deployed epicardially, the scope of this disclosure also includes endocardial options and intravenous options (e.g., as in the coronary veins). A novel scheme of pulsed-mode operation will allow quick attainment and short duration cooling that will terminate atrial fibrillation.

In one implementation, a cardiac treatment device includes an expandable mesh, and a plurality of cooling elements attached to the mesh. At least some of the plurality of cooling elements are electrically interconnected. The mesh is configurable in a low-profile delivery configuration for containment within a delivery sheath, and configurable in an expanded configuration for deployment on a cardiac tissue surface.

Such a cardiac treatment device may optionally include one or more of the following features. The plurality of cooling elements may comprise Peltier elements. The cardiac treatment device may further comprise two or more arms attached to the mesh. The two or more arms may be expandable to cause the mesh to reconfigure from the delivery configuration to the expanded configuration. The cardiac treatment device may further comprise an energy source. The energy source may be configured to operate in a pulse-mode for providing energy to the plurality of cooling elements. The energy source may be configured to operate in a biphasic waveform mode for providing energy to the plurality of cooling elements. At least some cooling elements of the plurality of cooling elements may be multiple Peltier elements that are sandwiched together. The cardiac treatment device may further comprise a fabric attached to the mesh. The fabric may be configured for suturing the cardiac treatment device to the cardiac tissue surface. The cardiac treatment device may further comprise one or more temperature monitoring devices attached to the mesh. The one or more temperature monitoring devices may include thermocouples.

In another implementation, a method of treating cardiac arrhythmia of a heart includes deploying a cardiac treatment device onto a tissue surface of the heart, and activating the cooling elements to deliver cooling to the tissue surface of the heart. The cardiac treatment device includes an expandable mesh, and a plurality of cooling elements attached to the mesh. At least some of the plurality of cooling elements are electrically interconnected. The mesh is configurable in a low-profile delivery configuration for containment within a delivery sheath, and configurable in an expanded configuration for deployment on a cardiac tissue surface.

Such a method of treating cardiac arrhythmia of a heart may optionally include one or more of the following features. The cardiac arrhythmia may be an atrial arrhythmia. The tissue surface may be an atrial tissue surface. The cardiac arrhythmia may be a ventricular arrhythmia. The tissue surface may be a ventricle tissue surface. The method may further include detecting (after the activating the cooling elements to deliver cooling to the tissue surface) that the ventricular arrhythmia still exists, and applying anti-tachycardia pacing to the heart. The method may further include detecting (after the applying anti-tachycardia pacing to the heart) that the ventricular arrhythmia still exists, and applying electroporation to the heart. The method may further include detecting (after the applying electroporation to the heart) that the ventricular arrhythmia still exists, and applying one or more low energy shocks to the heart while simultaneously cooling the heart using the cardiac treatment device. The method may further include detecting (after the applying one or more low energy shocks to the heart) that the ventricular arrhythmia still exists, and applying one or more standard defibrillation shocks to the heart while simultaneously cooling the heart or nerves of the heart using the cardiac treatment device.

Particular embodiments of the subject matter described in this document can be implemented to realize one or more of the following advantages. In some embodiments, heart conditions such as arrhythmias and others can be treated using the devices and methods provided herein. In some embodiments, arrhythmias can be treated by an implantable system for painlessly terminating arrhythmias. The devices and methods provided herein permit prompt termination of atrial fibrillation almost immediately after an episode begins (to prevent persistence) and is effective irrespective of patient age and comorbidities. In some cases, such conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
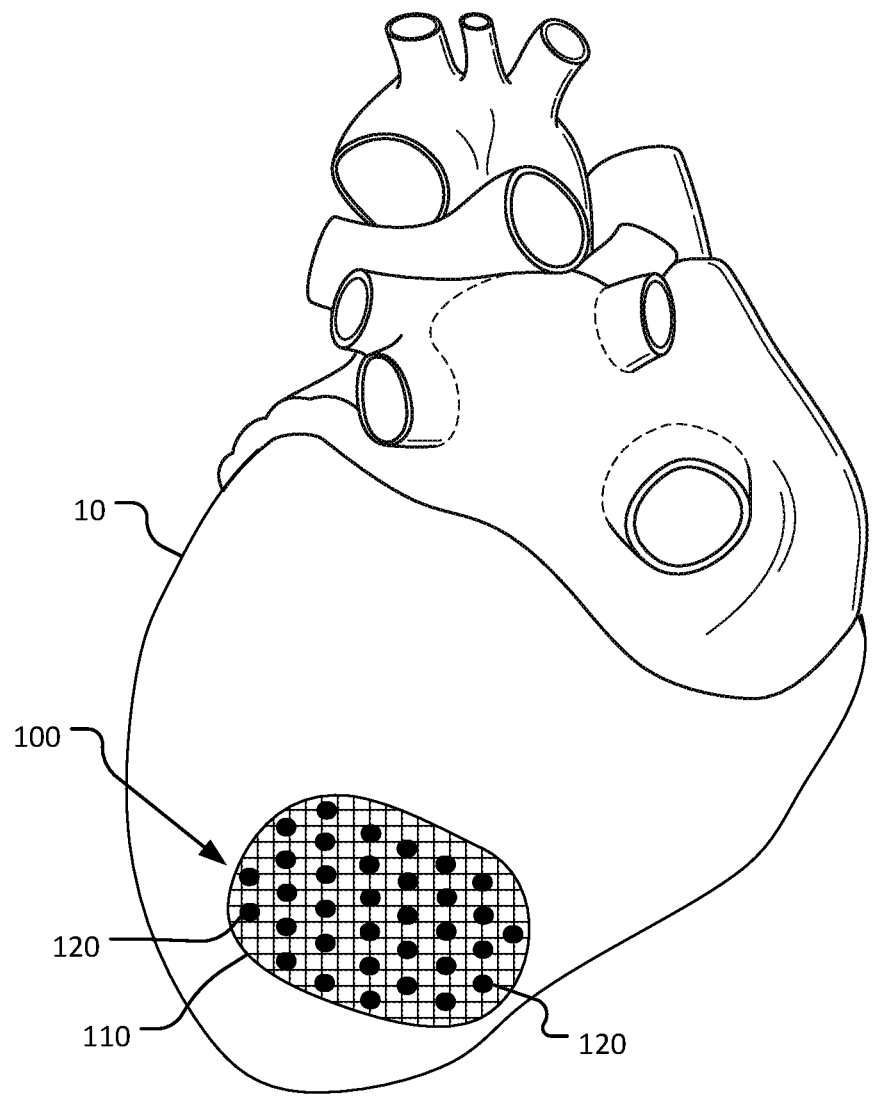
FIG. 1 is a schematic diagram of heart undergoing a thermal defibrillation treatment using a device in accordance with some embodiments provided herein.

This document provides devices and methods for the treatment of heart conditions. In particular, this document discloses devices and methods of defibrillation utilizing cold. For example, this document provides devices and methods for treating ventricular fibrillation (VF) by cooling the epicardium. As explained further below, the devices and methods provided herein can also be used to treat other disorders by applying heating and/or cooling to a patient (internally and/or externally) in a number of different advantageous manners.

Some embodiments provided herein include a percutaneously, epicardially placed defibrillator device capable of cooling the heart to 5-10 degrees Celsius. Such a device may include thermoelectric cooling elements that use the Peltier effect to create a heat flux between the junction of two different types of materials. In contrast to the more commonly used vapor-compression refrigeration, Peltier cooling elements require no moving parts or circulating refrigerants, have a near infinite life, and can be made of a small size and flexible shape. These elements become thermally active when a current is applied across them, with the temperature differential being a function of the current supplied into the system.

Thus, some embodiments provided herein consist of expandable epicardial leads that include multiple, small, electrically interconnected Peltier elements. In some embodiments, the Peltier elements may be minute (e.g., 1 mm×1 mm, or smaller) tiles conjoined to create a functional "cooling mesh," or larger tiles made of flexible materials. The mesh is connected to expanding arms that in a low profile arrangement would fit inside of a delivery sheath, and once in the pericardium would expand to deploy the cooling elements epicardially.

Alternatively, in some embodiments of the devices provided herein the cooling electrodes are less flexible than transcatheter devices and are configured to be surgically placed. Intra or extra-pericardial (but extracardiac) deployment of a cooling lead can be advantageous for several reasons. First, such a location poses little risk of intracardiac thrombus formation and thromboembolism. Second, the absence of circulating blood in the pericardial space facilitates cooling, as blood flow results in convective warming. Third, cooling of pericardial cardiac autonomic nerves and of epicardial coronary arteries may offer additional benefits, as described further herein.

In some embodiments, the deployable cooling electrode will also include multiple electrodes capable of pacing and sensing myocardium. Thus, even if VF is not fully terminated by cooling, its slowing and organization to ventricular flutter or tachycardia would render it susceptible to termination by essentially painless overdrive pacing. The conductive electrical components on the delivery frame would not only serve for pacing, but can be electrically conjoined to provide a sufficiently large electrode surface area to permit back up defibrillation. In some embodiments, a separate conductive member is present to permit defibrillation for back up when needed. Some iterations use a coiled cooling system that purposefully leaves complimentary coils of non-cooled myocardium to create an intra-myocardial thermal gradient that can be effective for defibrillation. In such a device, the coils will only need to be placed at critical areas of increased myocardial thickness or increased anisotropic myocardial fiber arrangement, or at the *nexus* points of the neural, Cajal's cells, and myocardial interface.

Some embodiments of the epicardially placed defibrillator devices include bipolar and/or unipolar recording electrodes. Such recording electrodes can function to detect and diagnose arrhythmia. In some embodiments, the recording can also function to detect and diagnose successful termination of arrhythmia. In addition, the electrodes may be used for mapping and creating templates of initiated arrhythmia episodes. In some embodiments, the epicardially placed defibrillator devices include components capable of delivering radiofrequency or direct current energy for permanent ablation of the mapped arrhythmia. The device's diagnostics for mapping an arrhythmia and/or ablation would be automated using a controller with pre-programmed templates. In some embodiments, delivery of ablation energy can also be automatically directed to the particular location of diagnosed arrhythmia origin following Peltier-based thermal/cooling termination of the atrial or ventricular fibrillation.

In some cases, combining low energy shock with cooling defibrillation may permit shocks to be essentially painless. In either the coiled or large surface area embodiments, and in a simultaneous or a sequential fashion, low energy shocks below the pain threshold can be delivered by the same surface as the Peltier cooling. The cooling can provide a complementary effect not only for defibrillation but for minimizing pain from the electroshock defibrillation. Similarly, the electroshock can provide a complementary effect on thermal cooling-induced loss of fibrillatory wave front conduction by creating intra-myocardial regions of block that break up reinitiating wave fronts of activation close to cooling.

As described herein, while a Peltier-based element cools on one side (the myocardial facing-side), the other side of the element warms. Several embodiments for dissipating or managing the heat on the non-cardiac side of the lead are envisioned herein. For example, one technique is the use of fins that sit within the pericardial space, or outside of the pericardial space, to capture the relative coolness of body temperature relative to the warm side of the Peltier electrode for heat dissipation. In some embodiments, fluid such as blood can be pumped or can passively flow along the fins (or allowed to circulate among the fins), which would be coated with an anticoagulant material to permit cooling. In another embodiment, the fins can be insulated to prevent significant heat dissipation into the surrounding structures. In some embodiments, the natural cooling effect of the lungs, which bring external air into the body, would be used for cooling.

In some embodiments, none of the Peltier-based element layers directly contact the epicardium, but the electrodes are affixed outside of the pericardium, in the mediastinum, mitigating the direct cold on the heart (with the pericardium acting as a thermal buffer), and the pleura provide cooling to the warm side of the element.

In some embodiments, Peltier elements can be sandwiched, or placed in series or parallel, permitting greater degrees of cooling on the cool side and greater separation spatially between the hot and the cold elements. Some embodiments include multilayered Peltier devices where the internal-most layer is the only one that has myocardial contact. The subsequent layers act as a cooling cascade to dissipate the heat generated from the first deployment in gradual stages such that the very last Peltier device is very close to body temperature. Single-layered material such as mono-layered graphene or mono-layered germane can allow potentially hundreds or thousands of such layers and require a differential cooling of less than 0.1° C.

In some embodiments, a Seebeck generator is paired with a Peltier device such that as soon as a temperature gradient is created at one layer of the Peltier device, the Seebeck generator that generates a voltage gradient that can be used to charge the capacitors, which in turn is used to create the initial cooling. Such a partially self-sustaining thermal circuit would reduce the need for battery capacity and thus minimize the size of the battery and capacitor. In some embodiments, alternating Peltier and Seebeck components are included. The Seebeck components would utilize the heat gradient in the layer superficial to the initial Peltier element to generate an electrical potential gradient that in turn would be used to power the next layer of the Peltier device. Such an arrangement will simultaneously allow offsetting the heat transfer and prevent battery drain by using the heat as an energy source.

In some cases, the time course of cooling can be germane in regard to defibrillation. In some embodiments, the use of special waveforms to rapidly alter temperature would be used. In some cases, the use of special waveforms can also permit management of the hot side of the element without the need for cooling fins or other mechanical heat management strategies (or in conjunction with such fins and/or strategies). One of the downsides of applying thermal insulation to the hot side of the Peltier element is that since the heat cannot dissipate, if flows back into the element itself and limits cooling. Use of a biphasic waveform would permit very rapid cooling, followed by reversal of the temperature gradient to neutralize both cold and hot sides of the Peltier element. In some cases, using this strategy, a thin layer of insulation on the hot side may suffice to permit rapid cooling without injury to the tissues on the hot side, and without the need for cooling fins or other heat dissipation mechanisms. In some embodiments, a large initial voltage and current would result in very rapid temperature differentials on both sides, which would then be reversed by a waveform of opposite polarity, rapidly rewarming the epicardial surface of the heart and eliminating the heat that had been developed on the warm side. A string of biphasic waveforms, separated by short intervals in time, or administered consecutively, may permit rapid temperature cycling and progressive rhythm termination, even if the first cooling cycle organizes but does not terminate the rhythm.

In some embodiments, the cooling may be intensified using a series of Peltier elements, with the cold side facing towards the myocardium in all of them, such that each successive element closer to the myocardium has its warm side cooled by its adjacent element. These elements could be energized sequentially (e.g., from the outside in, towards the heart) or in reverse, to optimize rapid cooling for rapid VF termination.

Other benefits and advantages exist with the use of cooling electrodes, intrinsic to the effects of cold on biological tissues, which provide other utilizations of the devices and methods provided herein. For example, application of cold in the pericardial space can be an effective treatment for ischemia. Detection of ischemia using electrocardiogramecorded changes on the electrical elements on the lead of some devices provided herein could be used to trigger a mild and controlled cooling of the coronary circulation or of the myocardial tissues, decreasing oxygen demand and treating ischemia. The development of incipient arrhythmias either by the detection of ischemia or increased ectopy can lead to mild cooling to minimize ectopy. In some cases, these techniques may prevent myocardial infarction or the development of lethal arrhythmias, rather than only treating arrhythmias after they have developed. Another device and method implementation provided herein includes cooling in, or just outside of, the pericardial space to cool the cardiac autonomic ganglia, thereby further treating and/or preventing arrhythmias.

In some embodiments, cooling elements are deployed within coronary veins or outside of the pericardial space and adjacent to the pleura. Elements placed within coronary veins would be deployed much as current coronary sinus leads are situated, with cooling elements arrayed facing towards the myocardium. In some embodiments, the layered Peltier elements are placed as a "lead" that will be anchored into the anterior intraventricular vein, a lateral vein, and a middle cardiac vein. The cooling will result in not only local cooling but use the returning venous collaterals as a cooling electrode. The specific layering can be in a hemicylindrical lead such that contact with the tissue will not be critical for the functioning of this device. Alternatively or additionally, a subxiphoid strategy that advances the lead without entering the pericardium, or that is intentionally directed towards the pleura, would benefit from the cooling effects of the pleura to mitigate the heat from the warm side of the lead surface.

In some embodiments, the devices and methods provided herein for cardiac application include an atrial defibrillator. In some cases, an atrial defibrillator can be placed in the pericardial space or extra-pericardially (e.g., assuming patients may already have pericardial adhesions). The device can be placed and slid under the left atrium in the vicinity of the oblique sinus, with another component that wraps around in a horseshoe shape over the transverse sinus and aortocaval space. Thus, a large surface area of the atrium will be cooled whenever atrial fibrillation is detected with integrated electrodes placed through a mesh-like Peltier device. A similar pericardial or extra-pericardial approach with plunge Peltier components can be used to treat ventricular defibrillation. In some embodiments, the superficial primary Peltier component can be positioned circumferentially around the plunge electrode which will be housed within the myocardium at sites where there are no coronary arteries. Similarly, in some cases this device can be used extra-pericardially for concurrent myocardial and neural element cooling.

Alternate uses beyond those mentioned above would include, but are not limited to, rapid cooling for obesity, heating or cooling post-surgery (e.g., to lessen pain, improve post-op course from comfort), cooling of blood for neural protection during acute stroke, and cooling of the pudendal veins for treating erectile dysfunction. Additional utilizations for the cooling technology provided herein also include wearable helmets that cool on impact to avoid injury in sports or combat situations, or external CNS cooling elements that are applied as a helmet to minimize brain injury in patients suffering from stroke, out of hospital cardiac arrest, or motor vehicle accidents. Still further applications for the devices and methods provided herein include treatment of seizure disorders, Parkinson's disorders, stroke, drownings, hypothermia, hyperthermia, head trauma, malignant hyperthermia (externally), heating or cooling during surgery, heating or cooling patients externally in hospital beds or at home, and as a catheter in the venous system for heating or cooling the body. Such devices can be implanted in a patient (temporarily or long term), positioned external to a patient (e.g., in a pad, clothing, bed, body wrap, helmet, etc.). In some cases, the heating component of the Peltier device may provide the therapeutic modality, and the sandwiching concept described herein can be used to dissipate the cooling.

Additional embodiments of the devices and methods provided herein (which can be either temporarily placed only when needed, or permanently implanted), is a system and method to cool the systemic circulation by using the cooling apparatuses described herein (e.g., shaped as a tubular structure and positioned within the transverse sinus of the pericardial spaces). An expandable tubular structure with the cooling elements in this region would be in direct proximity and in contact with both the ascending aorta and the pulmonary artery, thus cooling the entire forward circulation. A similar device and location but with the cooling elements directed inferiorly could be the primary implanted device when we are attempting to treat atrial fibrillation. Moreover, in regard to endovascular applications, in some embodiments a combined lead that is placed intra-vascularly can function as a defibrillator lead (e.g., has standard electrical coils) but also has Peltier elements embedded and adjacent to the ventricular septum and apex.

One feature of some embodiments provided herein, which enhances the secondary cooling of the Peltier elements, is an expandable, fan-like structure attached to the primary cooling element but placed external to the pericardium and within the subpleural or pleural space. In some embodiments, the intra-pericardial cooling component and the extra-pericardial secondary cooling component can be mated with each other by deflecting them both together, using electrodes to avoid the phrenic nerve (stimulating to be sure there is no phrenic capture), and the electrodes themselves being used to either weld or guide an attachment device like a button or a clip to maintain near-contiguous proximity of both the cardiac cooling and secondary Peltier cooling elements together.

In some embodiments, electrogram monitoring and analyses can be used to trigger an algorithm of sequential phasic cooling (e.g., whether or not a specific area shows ventricular fibrillation, or in the case of the atrium, atrial fibrillation, or regular electrical activity). The cooling algorithm can be phased to prioritize either the more regular areas or the more irregular areas. In some such embodiments of the devices and algorithms, when an implantable cardioverter defibrillator (ICD) is in place the intracardiac electrograms can also be used for the purpose of triggering a specific algorithm for phased cooling energy delivery.

In some embodiments provided herein, a cooling mesh includes multiple small cooling elements. In some such embodiments the cooling elements are Peltier devices. Such a configuration can be advantageous to permit the device to collapse into a sheath for percutaneous delivery, and to form fit epicardially around the heart for efficient energy delivery. In some such embodiments a "Peltier sandwich" arrangement is included, to multiply the cooling effects, and to mitigate external heating. In some embodiments, the devices provided herein are flexible mesh devices (by virtue of having multiple, small Peltier elements) that provide cooling throughout the device, and include conductive metal for electrical recording or energy delivery interdigitated throughout the mesh.

In general, current implantable cardiac defibrillators ("ICDs") do not analyze the morphology of premature ventricular contractions ("PVCs") or non-sustained runs. In all commercial devices, they first require the ventricular rate to be rapid enough to define it as a tachycardia, and then and only then do they assess morphology. This disclosure provides devices and methods for analysis of single PVCs or short events, that current ICDs ignore. A further distinction is that when ICDs assess morphology, they compare the tachycardia complex to a stored normal rhythm complex and then mathematically determine a match score (the means of doing so varies, but may use deviations from sample points or comparison of mathematical transforms of the waveform). If the rapid complex is different than the normal rhythm template, then the tachycardia is defined as ventricular (needs treatment), as opposed to supraventricular (don't treat). In contrast, the devices and methods provided herein include comparing single PVCs (or short runs) to that individual patient's PVCs that previously initiated tachycardia, or to known PVCs associated with VF (i.e. population and individual templates of complexes that initiate tachycardia). In other words, instead of comparing tachycardia to a "normal" template and treating if they are different, the devices and methods provided herein can treat with preventative interventions if the single beats are the same as those that previously caused arrhythmia. Moreover, the source of the electrograms would most likely (but not required to be) epicardial, providing a broader template (larger field electrogram, incorporating more data, thus, likely more accurate) of the PVCs.

Some embodiments of the devices and methods provided herein utilize a strategy of using cooling alone to prevent VF, or if ventricular tachycardia ("VT") or VF are present, to terminate them. Moreover, an additional goal is painless prevention of VF and/or termination of VF. In some embodiments, by using combinations of energy forms (e.g., cooling, electroporation, defibrillation) each can be used in a low enough dose so as to be fully painless. There is evidence, for example, that cooling of VF may organize it to VT when cooling doesn't fully terminate VF. In contrast to VF, VT can be terminated by antitachycardia pacing (which is not perceived at all, or may be felt as mild palpitations). Electroporation, using the devices and methods provided herein, may allow painless VF/VT termination, or more organize the rhythm. The same holds true for defibrillation-if the energy is low enough, it can be. Another strategy to prevent pain is to cool the nerves to the heart (rather than the heart) so that when a stimulus to restore rhythm is given that would otherwise be painful, it is not experienced as pain.

This disclosure provides implantable devices that achieve non-destructive rapid and temporary cooling of cardiac tissues for the termination, and potentially prevention, of atrial arrhythmias. The ion channels responsible for propagation of electrical wave fronts through myocardial tissue are temperature sensitive and temperature reduction terminates fibrillatory rhythms. The system includes a percutaneously placed expandable and simply deployed epicardial lead capable of cooling atrial tissues to between 5 to 10 degrees Celsius. The use of cold is particularly attractive due to its well-established safety record in cardiac applications. In some embodiments, the epicardial lead will be constructed using an array of thermal electric cooling elements that use the Peltier effect to create a heat differential between opposing surfaces. A novel scheme of pulsed-mode operation will allow quick attainment and short duration cooling that will terminate atrial fibrillation.

Referring to FIG. 1, some embodiments of the devices provided herein can be used to prevent, mitigate, or terminate fibrillatory rhythms of a heart 10. In the depicted embodiment, a thermal modification device 100 includes an expandable epicardial mesh 110 with leads that that include multiple small electrically-interconnected Peltier elements 120. In some embodiments, these Peltier elements 120 may be minute (e.g., 1 mm×1 mm or significantly smaller) tiles conjoined to create a functional "cooling mesh" or larger tiles made of flexible materials.

In some embodiments, the mesh 110 with an array of cooling elements 120 (e.g., thermal electric cooling elements that use the Peltier effect to create a heat differential between opposing surfaces) is connected to expanding arms and has a low-profile arrangement that fits inside a delivery sheath for percutaneous placement. Once in the pericardium, the device 100 expands to deploy the cooling elements 120 epicardially. In some embodiments, a scheme of pulsed-mode operation of the cooling elements 120 will allow quick attainment and short duration cooling that will terminate atrial fibrillation. Additionally, since arrhythmia termination only requires brief pulses of cold, a rapid, high-energy biphasic waveform can be used to rapidly cool then warm on the epicardial surface, with opposite temperature profile characteristics on the non-cardiac surface to mitigate potential discomfort. In some embodiments, shocks could be administered sequentially and with opposing polarities to really cool and then mitigate heart. Additionally, in some embodiments the lead system could be connected to a currently approved commercial system, using the biopic waveform to deliver cold (eliminating the need for a custom pulse generator for early generation devices).

In some embodiments provided herein, the device 100 includes modified Peltier cooling elements 120 with integrated thermocouples (or other types of temperature monitoring devices) for temperature registration, and the device 100 includes affixed fabric to permit surgical suturing of the cooling element device 100 to the myocardium of heart 10. In some embodiments, cooling fins are included on the Peltier cooling elements 120 to dissipate the heat.

In some cases, device 100 with Peltier cooling elements 120 is placed initially adjacent to the right and left atria, with thermocouples placed against the atrial myocardium beneath the Peltier elements 120 and adjacent to it. Additionally, in some cases a multipolar catheter can be placed in the right atrium to permit pacing and assessment of conduction velocity.

The devices for thermal defibrillation provided herein can be placed using a range of surgical devices and techniques. In some embodiments, the defibrillation device(s) is deployed percutaneously. The approach can be, for example, subxiphoidal, lateral, or transvenous. In some embodiments, video-assisted thoracoscopy can be used. In some embodiments, robotic assistance can be used. In some embodiments, open-chest techniques are used. In some embodiments, a combination of such techniques are used.

In some embodiments, a cutting of the pericardium is performed from the outside of the pericardium. Components for visualizing, probing, and sensing the anatomy may be included with the devices provided herein. For example, in some embodiments the devices provided herein include pacing electrode devices. In some embodiments, the devices provided herein include an impedance measurement probe for sensing tissue or nerves. In some embodiments, the devices provided herein include a Doppler probe for visualizing the anatomy. In some embodiments, the devices provided herein include a camera for providing images of internal anatomy. In some embodiments, the devices provided herein include thoracoscopy style devices.

Some embodiments of device 100 include bipolar and/or unipolar recording electrodes. Such recording electrodes can function to detect and diagnose arrhythmia. In some embodiments, the recording can also function to detect and diagnose successful termination of arrhythmia. In addition, the electrodes may be used for mapping and creating templates of initiated arrhythmia episodes. In some embodiments, the epicardially placed defibrillator devices include components capable of delivering radiofrequency or direct current energy for permanent ablation of the mapped arrhythmia. The device's diagnostics for mapping an arrhythmia and/or ablation would be automated using a controller with pre-programmed templates. In some embodiments, delivery of ablation energy can also be automatically directed to the particular location of diagnosed arrhythmia origin following Peltier-based thermal/cooling termination of the atrial or ventricular fibrillation.

In some embodiments, one or more Seebeck generators (not shown) is/are paired with a Peltier device 120 such that as soon as a temperature gradient is created at one layer of the device 100, the Seebeck generator that generates a voltage gradient that can be used to charge one or more capacitors, which in turn is used to supply energy for the initial cooling (of Peltier devices 120). Such a partially self-sustaining thermal circuit would reduce the need for battery capacity and thus minimize the size of the battery and capacitor. In some embodiments of device 100, alternating Peltier and Seebeck components are included. The Seebeck components would utilize the heat gradient in the layer superficial to the initial Peltier element 120 to generate an electrical potential gradient that in turn would be used to power the next layer of the Peltier device 120. Such an arrangement will simultaneously allow offsetting the heat transfer and prevent battery drain by using the heat as an energy source.

In some embodiments, various types of high specific heat materials may be placed as insulation within the layers of the device 100 and/or on the external surface of one or more of a single-layered Peltier element 120 to offset or mitigate adverse/unwanted heat transfer.

Figure 2:
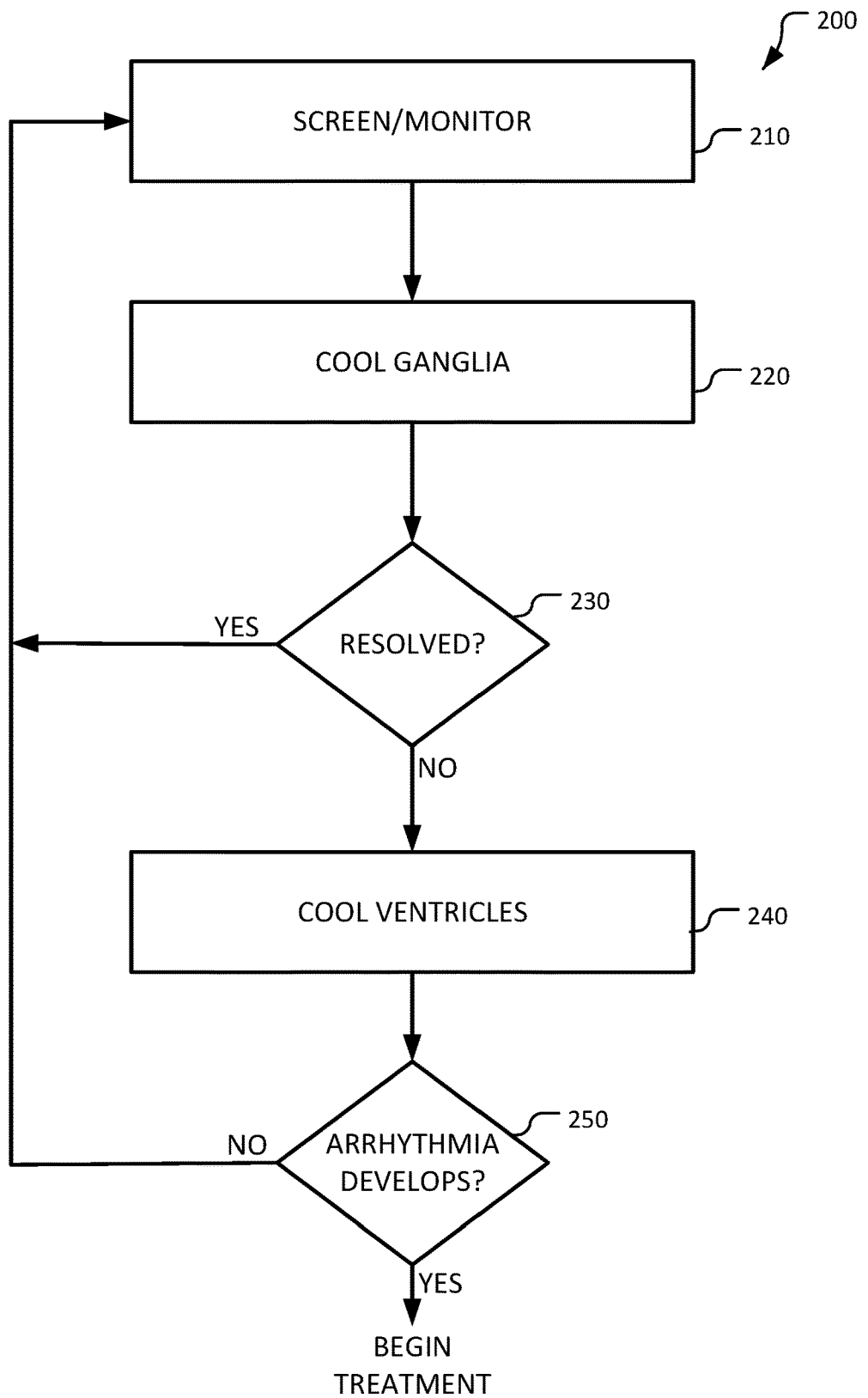
FIG. 2 is a flowchart of a method for preventing arrhythmias using cooling in accordance with some embodiments provided herein.

Referring to FIG. 2, in addition to cooling to terminate arrhythmias, cooling using the devices provided herein can be used as part of a method 200 to prevent arrhythmias. Atrial fibrillation typically begins with initiating triggers in the form of premature atrial complexes. As demonstrated in FIG. 2, the detection of atrial ectopy and incipient arrhythmias in operation 210 can be used to trigger cooling of ganglia in operation 220 and ventricles in operation 240 to prevent the onset of atrial fibrillation in step 250.

In some embodiments, a cooling device that is placed in the oblique sinus would be in juxtaposition to all four pulmonary veins, and such cooling may serve to prevent the exit of triggering foci that have been associated with arrhythmia as well as reentry at the venoatrial junction. It is also in proximity to the autonomic ganglia that have been associated with arrhythmogenesis. Given the painless nature of the cooling, such effects can be tolerated repeatedly. Moreover, the cooling elements would be coupled to electrically active pacing electrodes to permit antitachycardia pacing should cooling organize fibrillation to flutter without complete termination.

In some embodiments, recording electrodes are placed in either the oblique sinus or other regions in the atrium or atrioventricular annulus. In some cases, such recording electrodes will record and distinguish between ganglia activity, atrial activity, and ventricular activity. Abnormal ganglia activity may precede an arrhythmic episode. Thus, even before the rhythm disturbance fully occurs, cooling from the cooling devices described herein can be delivered to offset the arrhythmic episode.

Figure 3A:
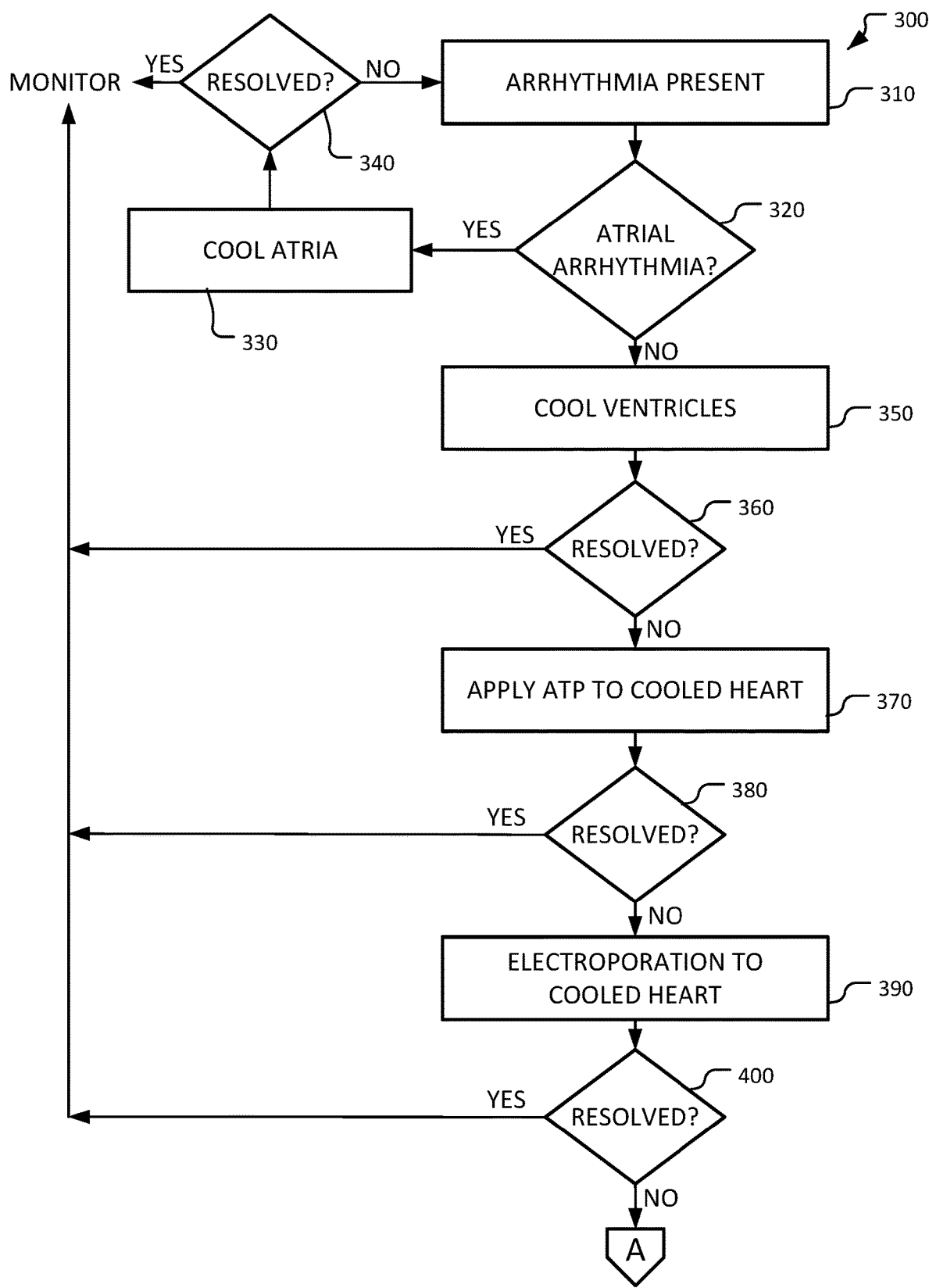
FIGS. 3A and 3B is a flowchart of a method for sequential administration of energy forms for painless prevention and termination of arrhythmias.
Figure 3B:
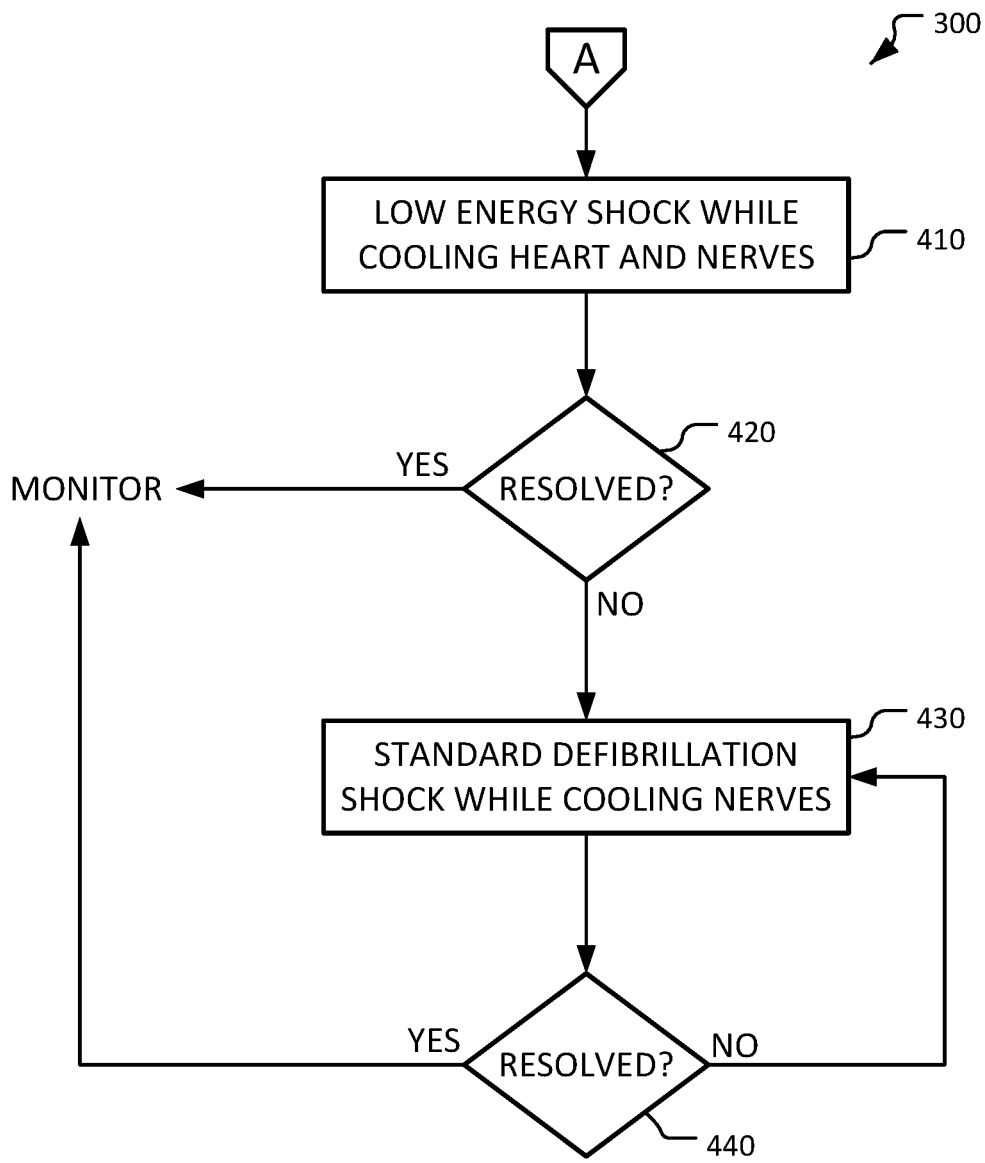

Referring to FIGS. 3A and 3B, a method 300 for sequential administration of energy forms to painless prevention and termination of arrhythmias is provided. In operation 310 a type of arrhythmia is detected. The arrhythmia may be any of the various types of cardiac arrhythmias. In operation 320 a determination is made as to whether the arrhythmia detected is an atrial arrhythmia. If the arrhythmia detected is an atrial arrhythmia, the atria are cooled in operation 330 using a cooling device and method provided herein. Thereafter, in operation 340, if the atrial arrhythmia is resolved the cooling can be ceased and monitoring can be performed. However, in operation 340, if the atrial arrhythmia is not resolved cooling of the atria can be repeated (operations 310 and 320).

If the arrhythmia detected is not an atrial arrhythmia, the ventricles are cooled in operation 350 using a cooling device and method provided herein. Thereafter, in operation 360, if the ventricular arrhythmia is resolved the cooling can be ceased and monitoring can be performed. However, in operation 360, if the ventricular arrhythmia is not resolved the method 300 can proceed to operation 370. At operation 370, anti-tachycardia pacing ("ATP") is applied to the cooled heart. Thereafter, in operation 380, if the ventricular arrhythmia is resolved the treatment can be ceased and monitoring can be performed. However, in operation 380, if the ventricular arrhythmia is not resolved the method 300 can proceed to operation 390.

In operation 390, electroporation can be performed/applied to the cooled heart. Such electroporation involves an application of DC energy to the epicardium. The result of the DC energy is a non-thermal cellular treatment that, in some cases, can resolve the arrhythmia. Thereafter, in operation 400, if the ventricular arrhythmia is resolved the treatment can be ceased and monitoring can be performed. However, in operation 400, if the ventricular arrhythmia is not resolved the method 300 can proceed to operation 410 shown in FIG. 3B. At operation 410, low energy shock can be applied while cooling the heart and the nerves of the heart. Such a treatment may resolve the arrhythmia. Thereafter, in operation 420, if the ventricular arrhythmia is resolved the treatment can be ceased and monitoring can be performed. However, in operation 420, if the ventricular arrhythmia is not resolved the method 300 can proceed to operation 430. In operation 430, standard defibrillation by electrical shocking, while cooling the cardiac nerves, can be performed. Thereafter, in operation 440, if the ventricular arrhythmia is resolved the treatment can be ceased and monitoring can be performed. However, in operation 440, if the ventricular arrhythmia is not resolved the method 300 can return to operation 430.

While this specification contains many specific implementation details, these should not be construed as limitations on the scope of any invention or of what may be claimed, but rather as descriptions of features that may be specific to particular embodiments of particular inventions.

Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for treating atrial fibrillation of a patient, the method comprising:

surgically placing, during an open-chest surgery, an expandable cooling device at least partially in an oblique sinus of the patient such that the cooling device is in juxtaposition to all four pulmonary veins of the heart, wherein the expandable cooling device comprises one or more recording electrodes;

surgically placing, during the open-chest surgery, the one or more recording electrodes in the oblique sinus of the patient;

after the open-chest surgery, detecting abnormal ganglia activity indicating atrial fibrillation of the patient using the one or more recording electrodes; and in response to the detection of the abnormal ganglia activity, delivering cooling from the cooling device to cool epicardial tissue of a heart of the patient to 5° C.-10° C. to prevent the exit of triggering foci and reentry at the venoatrial junction.

2. The method of claim 1, wherein the cooling delivery comprises pumping a fluid to the cooling device.

3. The method of claim 2, further comprising ceasing the pumping in response to resolution of the atrial fibrillation.

4. The method of claim 1, further comprising delivering pacing by the cooling device.

5. The method of claim 1, further comprising after the delivery of the cooling, monitoring for further occurrences of atrial fibrillation.

6. The method of claim 1, further comprising monitoring a temperature of the epicardial tissue using one or more temperature monitoring devices of the cooling device.

7. The method of claim 6, wherein the one or more temperature monitoring devices comprise thermocouples.

8. The method of claim 1, further comprising applying one or more standard defibrillation shocks to the heart while simultaneously delivering the cooling.

* * * * *